United States Patent
Hu et al.

(10) Patent No.: US 10,029,966 B2
(45) Date of Patent: Jul. 24, 2018

(54) METHOD AND REACTION EQUIPMENT FOR PREPARING DIMETHYL ETHER AND OLEFIN FROM METHANOL

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Shuai Hu, Shanghai (CN); Xin Jin, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 0 days.

(21) Appl. No.: 15/268,456

(22) Filed: Sep. 16, 2016

(65) Prior Publication Data

US 2017/0137357 A1    May 18, 2017

(30) Foreign Application Priority Data

Nov. 17, 2015    (CN) .......................... 2015 1 0537517

(51) Int. Cl.
| | | |
|---|---|---|
| *C07C 41/09* | (2006.01) | |
| *B01J 8/04* | (2006.01) | |
| *C07C 1/20* | (2006.01) | |
| *B01J 8/06* | (2006.01) | |

(52) U.S. Cl.
CPC ............ *C07C 41/09* (2013.01); *B01J 8/0453* (2013.01); *B01J 8/0457* (2013.01); *B01J 8/0492* (2013.01); *B01J 8/0496* (2013.01); *B01J 8/065* (2013.01); *C07C 1/20* (2013.01); *B01J 2208/00256* (2013.01); *B01J 2208/00548* (2013.01); *B01J 2208/027* (2013.01); *Y02P 20/52* (2015.11)

(58) Field of Classification Search
None
See application file for complete search history.

(56) References Cited

U.S. PATENT DOCUMENTS

| 2,014,408 A | 9/1935 | Woodhouse |
| 2012/0142973 A1 | 6/2012 | Su et al. |
| 2016/0107962 A1* | 4/2016 | Greager .............. C07C 29/1512 518/706 |

FOREIGN PATENT DOCUMENTS

| CN | 103813852 A | 5/2004 |
| CN | 101016231 A | 8/2007 |
| CN | 103421561 A | 12/2013 |
| CN | 103980083 A | 8/2014 |
| CN | 104508088 A | 4/2015 |
| DE | 3817816 A1 | 11/1989 |
| KR | 10-2010-0087388 | 8/2010 |

OTHER PUBLICATIONS

Ni et al, "Analysis to Length-Changeable Fixed Bed Reactor," Chemical Engineering (China), vol. 21, No. 3, Jan. 1993.

* cited by examiner

*Primary Examiner* — Rosalynd A Keys
(74) *Attorney, Agent, or Firm* — Duane Morris LLP

(57) ABSTRACT

The present invention relates to a method for preparing dimethyl ether from methanol which is carried out in a reaction device arranged with a plurality of catalyst bed layers connected in series, and comprises: dividing the reactant stream that contains methanol into n substreams, and feeding these different substreams into the reaction device through top feed ports or side feed ports between the catalyst bed layers of the reaction device for methanol-to-dimethyl ether reaction; wherein, the temperature T1 of the substream fed into the first catalyst bed layer is controlled within the following range: $290-50K1 \leq T1 \leq 150K1^2 - 271K1+397.5$; where, $1>K1 \geq 0.5$, and T1 is in unit of ° C.

7 Claims, 3 Drawing Sheets

METHOD AND REACTION EQUIPMENT FOR PREPARING DIMETHYL ETHER AND OLEFIN FROM METHANOL

CROSS REFERENCE TO RELATED APPLICATIONS

This application claims priority to Chinese Application No. 201510537517.9, filed on Nov. 17, 2015, entitled "Method for Preparing Dimethyl Ether from Methanol", the teaching of which is specifically and entirely incorporated herein by reference.

FIELD OF THE INVENTION

The present invention relates to a method for preparing dimethyl ether from methanol, a method for preparing olefin from methanol including the method for preparing dimethyl ether from methanol, reaction equipment for preparing dimethyl ether from methanol, and a system for preparing olefin from methanol.

BACKGROUND OF THE INVENTION

Fixed bed reactors are a sort of common reactors. In the most common design, a fixed bed reactor has one fixed bed layer or a plurality of fixed bed layers; in the case of a plurality of fixed bed layers, these fixed bed layers are in the same height, or the fixed bed layers are in an incremental height design in the material flow direction, and thereby the feed amounts at the stages are equal to each other or increase stage by stage in the material flow direction. In "Chemical Engineering" (p. 43-48, No. 3, Vol. 21, 1993), Jinfang N I and Kaihong Z H U et al have described a fixed bed reactor for preparing ethyl benzene from benzene and ethylene, which is designed on the basis of an ideal that the fixed bed layers are in the same height and the feed amounts at the stages are equal to each other; in contrast, in a fixed bed reactor for preparing dimethyl benzene from methyl benzene by methylation and the main fixed bed reactor in the apparatus of Lurgi (a German company) for preparing propylene from methanol, the bed layers are in an incremental height design, and thereby the feed amounts increase stage by stage.

Propylene is a basic organic chemical material in a great demand, and is mainly obtained from the petroleum processing process. As the petroleum resources are in short increasingly, more and more attention has been paid to the development of techniques for preparing propylene from non-petroleum resources such as coal or natural gas in China and foreign countries. The Methanol-To-Propylene (MTP) technique is a new technique that is the most hopeful substitute for the petroleum route. Preparing a synthetic gas from coal or natural gas and then preparing methanol and dimethyl ether from the synthetic gas is a matured technique. Hence, since preparing propylene from methanol is a key technique in the coal-to-olefin route, researches on the methods for preparing dimethyl ether from methanol have been made vigorously.

For example, the patent document U.S. Pat. No. 2,014,408 describes a method for preparing DME from methanol in the existence of a catalyst such as aluminum oxide, titanium oxide, and barium oxide, wherein, the reaction temperature is preferably 350-400° C. The patent document DE3817816 describes a method for preparing dimethyl ether from methanol by catalytic dehydration in a methanol synthesis apparatus, which utilizes a heat-insulated single-stage fixed bed reactor. The process flow chart of the above-mentioned method is shown in FIG. 1, wherein, a material fed at a flow rate F1 at temperature T0 is heated up to temperature T1 and then is fed into a catalyst bed layer BED1 in a reactor R1 for reaction.

The above-mentioned method employs a single-stage heat-insulated fixed bed reactor. Though the reactor structure is simple, the temperature rise in the catalyst bed layer is almost 130° C., and the hottest-spot temperature, which refers to the peak temperature in the catalyst bed layer in the axis, is almost 400° C.; consequently, the internal structure of the catalyst is unstable, the catalyst may be aged easily and the catalyst life may be shortened. In addition, since a single-stage fixed bed reactor is used, all feed material has to be heated up to an initiation temperature required for initiating the reaction in the heat-insulated catalyst bed layer; consequently, the energy consumption for the feed material is high. If the hottest-spot temperature is too low, the reaction will not be completed enough, and the conversion rate will not be high; if the hottest-spot temperature is too high, the reaction will be too violent and may be out of control; consequently, a vicious circle of temperature runaway, occurrence of severe subsidiary reactions, and further temperature rise may occur, not only resulting in material loss and equipment damage, but also causing collapsed catalyst skeletons and shortened catalyst life.

In recent years, the application of the MTP technique introduced from Lurgi (a German Company) in the coal-based olefin production project of Shenhua Ningxia Coal Group has marked a break-through in the industrial application of the methanol-to-propylene technique. The technique employs fixed bed reactors and a two-stage reaction process that incorporates pre-reaction and main reaction, wherein, the pre-reaction is a reaction in which the methanol is partially converted into dimethyl ether, while the main reaction is a reaction in which the product of the pre-reaction reacts further in a second reactor to generate propylene. Owing to the fact that the methanol-to-dimethyl ether reaction in the MTP technique of Lurgi is a strong exothermic reaction and the MTP technique employs single-stage fixed bed reactors, like the techniques in the prior art, the temperature difference is great and the hottest-spot temperature is high in the catalyst bed layer in the methanol-to-dimethyl ether reaction apparatus; consequently, the catalyst may be aged easily, the catalyst life may be shorted, and the energy consumption for the feed material is high.

The patent document CN103813852A discloses a controlled cooling reactor for preparing dimethyl ether from methanol. First, the material is fed into a heat-insulated catalyst bed layer in a reactor to initiate the reaction; then, the material passes through a moderating zone, in which the material is cooled by direct or indirect heat exchange; finally, the material passes through a heat-insulated catalyst bed that serves as a conditioning zone and flows out of the reactor. The moderating zone employs a tubular reactor, in which heat exchange can be executed by direct-flow heat exchange or counter-flow heat exchange or liquid methanol can be injected as a liquid medium. Though the method effectively controls the hottest-spot temperature in the reaction and utilizes the reaction heat, the reactor design and manufacturing is quite complex, the catalyst charging is very time-consuming; especially, in the moderating zone, where the tubular reactor is located between two fixed beds, the catalyst charging is more labor-intensive and time-consuming. In addition, all feed material has to be heated up to an initiation temperature required for initiating the reaction in the heat-insulated catalyst bed layer; consequently, the energy consumption for the feed material is high.

SUMMARY OF THE INVENTION

To overcome the drawbacks in the prior art, such as high temperature difference and high hottest-spot temperature in the catalyst bed layer, catalyst aging, shortened catalyst life, and high energy consumption for the feed material, etc., the present invention provides a novel method for preparing dimethyl ether from methanol, a novel method for preparing olefin from methanol including the method for preparing dimethyl ether from methanol, reaction equipment for preparing dimethyl ether from methanol, and a system for preparing olefin from methanol including the reaction equipment. When the method is used to prepare dimethyl ether from methanol, it has advantages including lower temperature difference and lower hottest-spot temperature in the catalyst bed layer, catalyst aging resistance, long catalyst life, and lower energy consumption for the feed material, etc.

To solve the above-mentioned technical problems, in a first aspect of the present invention, a method for preparing dimethyl ether from methanol carried out in a reaction device arranged with a plurality of catalyst bed layers connected in series is provided, comprising: dividing a reactant stream that contains methanol into n substreams, and feeding these different substreams of the reactant into the reaction device through top feed ports or side feed ports between the catalyst bed layers of the reaction device for methanol-to-dimethyl ether reaction; in addition, according to the flow directions of the streams of reactant, the flow rates of then substreams are F1~Fn respectively, the allocation proportions $K_i$ of the reactant in the substreams are Fi/F0, wherein, F0 is the sum of F1~Fn, i is an integer in the range of 1~n, and n is a integer greater than 1, wherein, the temperature T1 of the substream fed into the first catalyst bed layer is controlled within the following range:

$$290-50K1 \leq T1 \leq 150K1^2 - 271K1 + 397.5;$$

wherein, $1 > K1 \geq 0.5$, and T1 is in unit of ° C.

According to a preferred embodiment of the present invention, $2 \leq n \leq 8$, preferably $2 \leq n \leq 6$.

According to a preferred embodiment of the present invention, $0.95 \geq K1 \geq 0.6$, preferably $0.9 \geq K1 \geq 0.6$.

According to a preferred embodiment of the present invention, $1 > K1 \geq 0.6$, preferably $0.95 \geq K1 \geq 0.7$, more preferably $0.9 \geq K1 \geq 0.75$.

According to a preferred embodiment of the present invention, the allocation proportion $K_i$ of the reactant in the substream i is $Ki \geq (1-\Sigma_{i=1}^{i-1}K_i) \times 50\%$, preferably $Ki \geq (1-\Sigma_{i=1}^{i-1}K_i) \times 60\%$, more preferably $Ki \geq (1-\Sigma_{i=1}^{i-1}K_i) \times 70\%$, wherein, $i \neq 1$.

According to a preferred embodiment of the present invention, the reaction device comprises one or more fixed bed reactors, with a plurality of catalyst bed layers arranged in said one or more fixed bed reactors.

According to a preferred embodiment of the present invention, the reaction device comprises one fixed bed reactor, with a plurality of catalyst bed layers arranged in the same fixed bed reactor.

The reaction device comprises a plurality of fixed bed reactors, with one catalyst bed layer arranged in each fixed bed reactor.

In a second aspect of the present invention, a reaction apparatus for preparing dimethyl ether from methanol is provided, comprising a feeding device, a flow control device, a heating device, and a reaction device, wherein, the reaction device is arranged with a plurality of catalyst bed layers in it, the feeding device is configured to provide a methanol-containing gas-phase material to at least two of the catalyst bed layers, the flow control device is arranged between the feeding device and the reaction device and is configured to at least control the amount of the gas-phase material entering into the first catalyst bed layer, the heating device is arranged between the feeding device and the first catalyst bed layer in the flow direction of the gas-phase material and is configured to heat up the methanol-containing gas-phase material fed to the first catalyst bed layer, wherein, the feeding device is a gas-phase feeding device, and the catalyst that forms the catalyst bed layer is a catalyst for preparing dimethyl ether from methanol.

According to a preferred embodiment of the present invention, no heating device is arranged between the gas-phase feeding device and any other catalyst bed layer.

According to a preferred embodiment of the present invention, the flow control device is a flow valve.

According to a preferred embodiment of the present invention, $2 \leq n \leq 8$, preferably $2 \leq n \leq 6$.

According to a preferred embodiment of the present invention, the reaction device comprises one or more fixed bed reactors, with said n catalyst bed layers arranged in the one or more fixed bed reactors.

Preferably, the reaction device comprises one fixed bed reactor, with said n catalyst bed layers arranged in the same fixed bed reactor; or the reaction apparatus comprises n fixed bed reactors, with one catalyst bed layer arranged in each fixed bed reactor.

In a third aspect of the present invention, a method for preparing olefin from methanol is provided, comprising: preparing dimethyl ether from methanol with the above-mentioned method, and then controlling the reaction product obtained from the previous reaction to react to prepare olefin under conditions for preparing olefin from dimethyl ether.

According to a preferred embodiment of the present invention, the conditions for preparing olefin from dimethyl ether include: 390~650° C. reaction temperature, 0.01~2.00 MPaG pressure, and 0.2~6.0 h−1 mass space velocity of the reaction product.

According to a preferred embodiment of the present invention, the reaction for preparing olefin is carried out in a fixed bed reactor that comprises at least two conversion zones, wherein, counted from top to bottom, the first conversion zone comprises gas distribution elements and catalyst bed layers, and the second conversion zone and other conversion zones comprise gas distribution elements, liquid atomization elements, and catalyst bed layers; the reaction of preparing olefin from the reaction product obtained from the previous reaction under the conditions for preparing olefin from dimethyl ether comprises: dividing into the product obtained from the previous reaction into a plurality of streams, heating up the first gas-phase stream and then feeding it via the gas distribution elements into the first conversion zone, while directly feeding the rest gas-phase streams via the gas distribution elements into the second conversion zone and other conversion zones without heating or cooling; and feeding a liquid-phase chilling material via the liquid atomization elements into the second conversion zone and other conversion zones.

Preferably, the weight ratio of the first gas-phase stream to the reaction product obtained from the reaction is 0.08~0.20.

In a forth aspect of the present invention, a system for preparing olefin from methanol is provided, comprising a unit for preparing dimethyl ether from methanol and a unit for preparing olefin from dimethyl ether, wherein, a discharge port of the unit for preparing dimethyl ether from methanol communicates with a feed port of the unit for preparing olefin from dimethyl ether, and the unit for preparing dimethyl ether from methanol is the above-mentioned reaction apparatus for preparing dimethyl ether from methanol.

According to a preferred embodiment of the present invention, the unit for preparing olefin from dimethyl ether comprises a reaction device for preparing olefin and a liquid-phase chilling material feeding device, wherein, the reaction device for preparing olefin comprises at least two conversion zones, wherein, counted from top to bottom, the first conversion zone comprises gas distribution elements and catalyst bed layers, and the second conversion zone and other conversion zones comprise gas distribution elements, liquid atomization elements, and catalyst bed layers; the liquid-phase chilling material feeding device communicates with the liquid atomization elements and feeds the material to the liquid atomization elements.

According to a preferred embodiment of the present invention, the system further comprises: a flow valve arranged between the unit for preparing dimethyl ether from methanol and the unit for preparing olefin from dimethyl ether and configured to control the amount of the material from the unit for preparing dimethyl ether from methanol into the conversion zones; and a heater arranged between the unit for preparing dimethyl ether from methanol and the unit for preparing olefin from dimethyl ether and configured to heat up the material entering into the first conversion zone (including the material from the unit for preparing dimethyl ether from methanol), so that the material reaches to a desired temperature.

According to a preferred embodiment of the present invention, the conversion zones are in quantity of 2~8 zones.

According to a preferred embodiment of the present invention, the catalyst that forms the catalyst bed layers in the reaction device for preparing olefin is a SAPO molecular sieve.

The above-mentioned method provided in the present invention provides a reliable quantitative data support for the temperature control in the reactor for preparing dimethyl ether from methanol; in addition, during reactor startup and operation, the target temperature of the material in the first reaction zone of the reactor can be determined conveniently and quickly according to the proportion of material allocated to the first reaction zone; once the material allocation proportion for the first reaction zone is determined, the material allocation proportions for the rest reaction zones can be determined easily; thus, the feed material allocation proportions for all of the reaction zones in the entire reactor can be determined, and the startup and operation process becomes very simple. In addition, it is unnecessary to use any additional heat source or cold source to control the temperatures of the catalyst bed layers in the startup and operation process.

The above-mentioned methods provided in the present invention provides precise reference data for the startup and operation of the reactor for preparing dimethyl ether from methanol. Thus, there is a clear direction of adjustment in the control and adjustment of the temperatures in the reaction zones, and thereby the control and adjustment of the temperatures in the reaction zones is more convenient and easier.

With the above-mentioned method provided in the present invention, under the same conditions, the hottest-spot temperatures in the reaction zones are apparently lower than the corresponding hottest-spot temperatures attained with the methods disclosed in U.S. Pat. No. 2,014,408 and DE3817816. For example, the reactor outlet temperatures in the embodiments are lower than the reactor outlet temperatures in the Comparative Examples by 12~50° C., and the hottest-spot temperatures in the catalyst bed layers are lower by approx. 12~50° C.; thus, the temperature rises in the beds are lower by approx. 12~50° C., and a temperature runaway phenomenon in the beds can be prevented effectively, catalyst aging can be slowed down, and the catalyst life can be prolonged. In industrial production, an optimal point in the method provided in the present invention is used as the normal operating point of the apparatuses; therefore, the effect is better, and the hottest-spot temperature is decreased from approx. 390° C. to approx. 340° C.; thus, the hottest-spot temperature is decreased as far as possible on the premise of ensuring the conversion rate of methanol, the catalyst is protected effectively, and the catalyst life is maximized; in addition, since the feed amount F1 of the material to be heated up to the reaction temperature is lower than F0 (i.e., K1<1) with the method provided in the present invention, the heating load is decreased to attain an equivalent feeding temperature; hence, the energy consumption for the feed material is lower, and the energy is saved.

BRIEF DESCRIPTION OF DRAWINGS

The accompanying drawings are provided here to facilitate further understanding on the present invention, and constitute a part of this document. They are used in conjunction with the following embodiments to explain the present invention, but shall not be comprehended as constituting any limitation to the present invention. Among the drawings.

Figure 1:
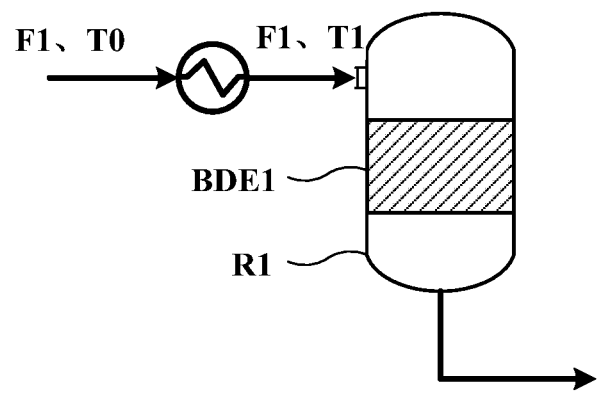
FIG. 1 is a schematic flow chart of the method for preparing dimethyl ether from methanol in the prior art.

Other features and advantages of the present invention will be further detailed in the embodiments hereunder.

DETAILED DESCRIPTION OF THE EMBODIMENTS

Hereunder some embodiments of the present invention will be detailed. It should be appreciated that the embodiments described here are only provided to describe and explain the present invention, but shall not be deemed as constituting any limitation to the present invention.

The ends points and any value in the ranges disclosed in the present invention are not limited to the exact ranges or values. Instead, those ranges or values shall be comprehended as encompassing values that are close to those ranges or values. For numeric ranges, the end points of the ranges, the end points of the ranges and the discrete point values, and the discrete point values can be combined to obtain one or more new numeric ranges, which shall be deemed as having been disclosed specifically in this document. In the following text, in principle, the methods may also be combined with each other to obtain new methods, which shall also be deemed as having been disclosed specifically in this document.

For the convenience of description, in the present invention, a catalyst bed layer is also referred to as a reaction zone, regardless of whether the n catalyst bed layers are arranged in one reactor or in a plurality of reactors.

In the present invention, the material entering into the reactor from the same catalyst bed layer is deemed as the same substream, regardless of whether the material enters into the reactor through the same port or not. For example, if there are a plurality of feed ports on the sides above a catalyst bed layer, the material entering into the reactor through these feed ports is deemed as the same substream, since the material enters into the same catalyst bed layer firstly.

In the present invention, the terms that are used to represent directions, such as "top", "bottom", "top part", and "bottom part", etc., are defined with reference to the material flow direction.

In the present invention, the first catalyst bed layer refers to the catalyst bed layer that comes into contact with the reactant firstly among the catalyst bed layers, despite of whether the catalyst bed layer is the first catalyst bed layer or not in terms of the physical position; however, the first catalyst bed layer is preferably the first catalyst bed layer in terms of the physical position.

The method for preparing dimethyl ether from methanol provided in the present invention is carried out in a reaction device arranged with a plurality of catalyst bed layers connected in series, and comprises: dividing the reactant stream that contains methanol into n substreams, and feeding these different substreams into the reaction device through top feed ports or side feed ports between the catalyst bed layers of the reaction device for methanol-to-dimethyl ether reaction; in addition, according to the flow directions of the reactant stream, the quantities of the n substreams are F1~Fn respectively, the allocation proportions Ki of the reactant in the substreams are Fi/F0, wherein, F0 is the sum of F1~Fn, i is an integer in the range of 1~n, and n is a integer greater than 1, wherein, the temperature T1 of the substream fed into the first catalyst bed layer is controlled within the following range:

$$290-50K1 \le T1 \le 150K1^2 - 271K1 + 397.5$$

where, $1 > K1 \ge 0.5$, and T1 is in unit of °C.

The reaction products pass through the last catalyst bed layer and are discharged from the reactor together finally.

As described above, in the conventional method for preparing dimethyl ether from methanol, the reaction temperature is judged and adjusted merely on the basis of the empirical value. Usually, the temperature of the feed material is adjusted while the material fed into the first reaction zone (i.e., the first catalyst bed layer) is increased; then, the temperature of the material fed into the first reaction zone is adjusted according to the reaction temperature in the first reaction zone. Since the reaction temperature is hysteretic, i.e., the effect of adjustment will exhibit only after a while from the time the temperature of the material fed into the first reaction zone is adjusted, a lot of time has to be spent to adjust again if the effect of adjustment is unsatisfactory or the direction of adjustment is wrong. Such a repeated adjustment process may easily result in high temperature difference, high hottest-spot temperature, temperature runaway, or over-temperature, etc., in some catalyst bed layers, and thereby may cause catalyst aging and shortened catalyst life, etc. Therefore, the conventional method may easily result in temperature runaway in the catalyst bed layers, and a lot of time has to be spent to find out an appropriate temperature point. The method disclosed in the present invention provides a precise data reference for the startup and operation of the methanol-to-dimethyl ether process. Hence, there is a clear direction of adjustment in the control and adjustment of the temperatures in the reaction zones, and thereby the problems such as high temperature difference and high hottest-spot temperature in the catalyst bed layers, catalyst aging, and shortened catalyst life, etc., can be solved effectively; in addition, the control and adjustment of the temperatures in the reaction zones is more convenient and easier, and the energy consumption for the feed material is greatly reduced.

The method disclosed in the present invention is applicable to various methanol-to-dimethyl ether processes that employs a plurality of (more than two) catalyst bed layers, as long as the number of the catalyst bed layers is not less than 2. In the present invention, the number of the catalyst bed layers may be equal to or greater than the number of the streams of reactant, as long as different streams of reactant can enter into the reaction device from different catalyst bed layers for methanol-to-dimethyl ether reaction. In the present invention, it should be noted that the reactant entering into the reaction device from different catalyst bed layers are referred to as different substreams, while the reactant entering into the reaction device from the same catalyst bed layer is referred to as the same substream, that is to say, reactant fed through different ports may be referred to as the same substream, as long as these reactants come into contact with the same catalyst bed layer firstly.

Preferably, the number n of the substreams meets $2 \le n \le 8$, for example, n may be 2, 3, 4, 5, 6, 7 or 8, preferably $2 \le n \le 6$, more preferably $2 \le n \le 3$.

According to the method for preparing dimethyl ether from methanol provided in the present invention, the object of the present invention can be attained as long as the temperature T1 of the material entering into the first catalyst bed layer is controlled to be within the temperature range obtained under the condition of $1 > K1 \ge 0.5$, such as K1 is 0.55, 0.56, 0.57, 0.58, 0.59, 0.6, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95; however, preferably $0.95 \ge K1 \ge 0.6$, more preferably $0.9 \ge K1 \ge 0.6$.

According to another preferred embodiment of the present invention, $1 > K1 \ge 0.6$, preferably $0.95 \ge K1 \ge 0.7$, more preferably $0.9 \ge K1 \ge 0.75$.

In view that the first substream accounts for 50% or more in the total amount of the feed material (reactant stream), theoretically, the problem of temperature runaway and local hot point can be solved effectively as long as the proportion and feeding temperature of the first material stream is controlled properly; however, according to a preferred embodiment of the present invention, by further controlling the feed material allocation proportions for other reaction zones, the materials in the reaction zones can have reaction at more appropriate temperatures. Preferably, the feed material allocation proportion Ki for the reaction zone i after the first reaction zone is $Ki \ge (1 - \Sigma_{j=1}^{i-1} K_j) \times 50\%$, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, more preferably $Ki \geq (1-\Sigma_{i=1}^{i-1}K) \times 60\%$, such as 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, further more preferably $Ki \geq (1-\Sigma_{i=1}^{i-1}K) \times 70\%$, such as 70.5%, 71%, 71.5%, 72%, 72.5%, 73%, 73.5%, 74%, 74.5%, 75%, 75.5%, 76%, 76.5%, 77%, 77.5%, 78%, 78.5%, 79%, 79.5%, 80%, 80.5%, 81%, 81.5%, 82%, 82.5%, 83%, 83.5%, 84%, 84.5%, 85%, 85.5%, 86%, 86.5%, 87%, 87.5%, 88%, 88.5%, 89%, 89.5%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or 100%.

In the present invention, $\Sigma_{i=1}^{i-1}K$ means the sum of allocation proportions from K1 to K(i-1). Similarly, $1-\Sigma_{i=1}^{i-1}K$ means the left allocation proportions after K(i-1).

By controlling T1 and the allocation proportions Ki especially K1 of the substreams, it is unnecessary to additionally control the feeding temperatures of the rest streams of reactant, as long as the feeding is gas-phase feeding. Generally, the feeding temperatures of the other streams of reactant are 90~200° C., preferably are 98~180° C., depending on the previous processing step. Usually, for large-scale apparatuses, the temperature T0 of the material from the previous processing step is higher, usually is 150~180° C.; for small-scale apparatuses, the temperature T0 of the material from the previous processing step is lower, usually is 98~130° C. The method for preparing dimethyl ether from methanol provided in the present invention can process the material fed from a large-scale apparatus described above and the material fed from a small-scale apparatus described above.

It is seen from the above definition of the allocation proportions: the feed amounts of the reactant in the present invention decrease stage by stage; in addition, in the flow direction of the reactant stream, the feed amount of each substream is not less than the total amount of the reactant after this substream, namely, the feed amount of each substream is not less than 50% of the total amount of this substream and the follow-up substream, preferably not less than 60%. In the present invention, a decrement feeding scheme is used, mainly owing to the following consideration: since the reaction is a strong exothermic reaction and an equilibrium reaction, an optimal tradeoff between the thermal equilibrium of the reaction and the optimum working temperature range of the catalyst can be attained with the above-mentioned decrement feeding scheme.

Figure 2:
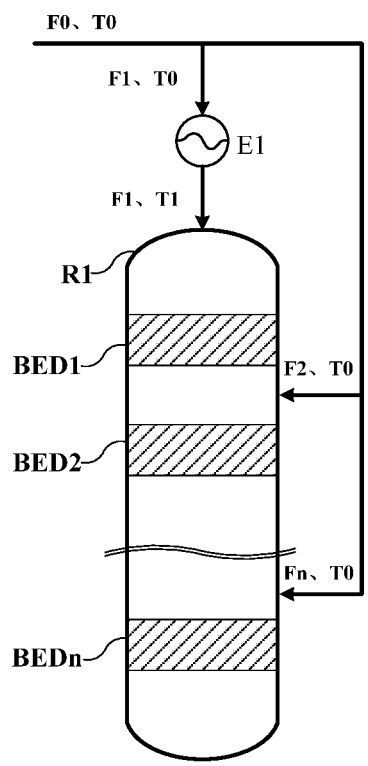
FIG. 2 is a schematic flow chart of one embodiment of the method for preparing dimethyl ether from methanol according to the present invention.
Figure 3:
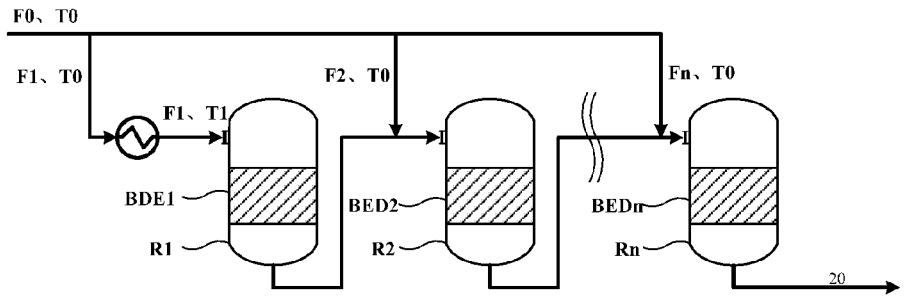
FIG. 3 is a schematic flow chart of another embodiment of the method for preparing dimethyl ether from methanol according to the present invention.

In the present invention, the catalyst bed layers may be loaded into the same reactor or loaded into different reactors, as long as they are connected in series. Namely, the reaction device in the present invention may comprise one or more fixed bed reactors, with n catalyst bed layers arranged in one or more fixed bed reactors. According to a preferred embodiment of the present invention, as shown in FIG. 2, the reaction device comprises one fixed bed reactor, with the catalyst bed layers BED1, BED2, . . . , BEDn loaded into the same reactor. According to a preferred embodiment of the present invention, as shown in FIG. 3, the reaction device comprises n fixed bed reactors, with catalyst bed layers BED1, BED2, . . . , BEDn loaded into different reactors R1, R2, . . . , Rn; preferably, one catalyst bed layer is loaded in each reactor. The reactor may be any fixed bed reactor that can be used to prepare dimethyl ether from methanol.

To obtain a desired temperature T1, as shown in FIGS. 2 and 3, a heat exchanger E1 is arranged before the first catalyst bed layer, to preheat the substream at temperature T0 to the temperature T1 before it is fed into the BED1.

According to the present invention, the operations and processing conditions for preparing dimethyl ether from methanol may be determined with reference to the prior art.

According to a preferred embodiment of the present invention, the heights of the catalyst bed layers are 500~4,000 mm. More preferably, the heights of the catalyst bed layers are 600~3,800 mm, further more preferably are 800~3,600 mm. The heights of the catalyst bed layers may be the same or different from each other.

According to a preferred embodiment of the present invention, the mass space velocity of the first stream of reactant in relation to the first catalyst bed layer is 0.5~5.0 h-1, preferably is 1.0~3.5 h-1.

The space velocities of the material feeding to the catalyst bed layers may be the same or different from each other, and may be 0.5~5.0 h-1 respectively, preferably is 1.0~3.5 h-1 respectively.

According to a preferred embodiment of the present invention, the pressure in the reaction device is 0.1~2.0 MPaG.

The catalyst that forms the catalyst bed layers may be any catalyst commonly used in the art, such as one or more of modified aluminum oxide and modified molecular sieve. For example, the modified aluminum oxide may be aluminum oxide modified by a rare earth metal in the Lanthanide series, and the modified molecular sieve may be a molecular sieve modified by rare earth metal and phosphate. For example, the rare earth metal in the Lanthanide series may be one or more of La, Ce, Pr, Nd, Pm, Sm, Eu, Gd, Tb, Dy, Ho, Er, Tm, Yb, and Lu. For example, the rare earth metal may be one or more of Sc, Y, La, Ce, Pr, Nd, Pm, Sm, Eu, Gd, Tb, Dy, Ho, Er, Tm, Yb and Lu. Preferably, the silica-alumina mole ratio of the molecular sieve modified by the rare earth metal and phosphate is 20~1,000, more preferably is 200~500. For example, specifically, the catalyst may be one or more of SMAP-500 series and SMAP-100 series from SINOPEC Shanghai Research Institute of Petrochemical Technology and DME-1 from Lurgi (a German company).

According to the method for preparing dimethyl ether from methanol provided in the present invention, the method doesn't include a step of controlling the temperatures in the catalyst bed layers by virtue of an additional cold source or heat source.

According to a preferred embodiment of the present invention, the method for preparing dimethyl ether from methanol provided in the present invention may employ the process flow shown in FIGS. 2 and 3: The total feed material at temperature T0 is divided into n substreams, the first substream in flow rate of F1 is fed into the heat exchanger E1, heated up to temperature T1 in the heat exchanger E1, and then fed into the first reaction zone BED1 for reaction; after the reaction is completed, the material discharged from the first reaction zone is mixed with the second substream in flow rate of F2, and the mixed material is fed into the second reaction zone BED2 for reaction; after the reaction is completed, the material discharged from the second reaction zone is mixed with the third substream, and the mixed material is fed into the third reaction zone for reaction, and so on, till the reactant reacts completely in the nth reaction zone and then is discharged from the reactor.

As shown in FIGS. 2 and 3, the difference between FIG. 2 and FIG. 3 only lies in whether a plurality of catalyst bed layers is loaded in one reactor or a plurality of reactors.

According to the method for preparing dimethyl ether from methanol provided in the present invention, the raw material methanol may be pure methanol (i.e., industrial methanol with purity higher than 99 mass %) or hydrous methanol (preferably the water content is lower than 20 mass %), or methanol that contains other impurities, as long as those impurities don't have an impact on the methanol-to-dimethyl ether reaction. In view that the hottest-spot temperature can be decreased if the raw material contains some water, preferably hydrous methanol is used in the present invention. With comprehensive consideration of the hottest-spot temperature and the reaction energy, preferably the water content in the raw material methanol is lower than 18 mass %, more preferably is lower than 10 mass %, further more preferably is lower than 8 mass %.

In a second aspect of the present invention, a reaction apparatus for preparing dimethyl ether from methanol is provided, comprising a feeding device, a flow control device, a heating device, and a reaction device, wherein, the reaction device is arranged with a plurality of catalyst bed layers in it, the feeding device is configured to provide a methanol-containing gas-phase material to at least two of the catalyst bed layers, the flow control device is arranged between the feeding device and the reaction device and is at least configured to control the amount of the gas-phase material entering into the first catalyst bed layer, the heating device is arranged between the feeding device and the first catalyst bed layer in the flow direction of the gas-phase material and is configured to heat up the methanol-containing gas-phase material fed to the first catalyst bed layer, wherein, the feeding device is a gas-phase feeding device, and the catalyst that forms the catalyst bed layer is a catalyst for preparing dimethyl ether from methanol.

Since the catalyst for preparing dimethyl ether from methanol has been described above, it will not be described anymore here.

According to the above-mentioned method provided in the present invention, as long as the temperature and allocation proportion of the material fed to the first catalyst bed layer is controlled properly, the object of the present invention can be attained, without controlling the temperature of the gas-phase material fed to the rest catalyst bed layers. Therefore, in the reaction apparatus provided in the present invention, no heating device is arranged between the gas-phase feeding device and any other catalyst bed layer.

According to a preferred embodiment of the present invention, a plurality of flow control devices is arranged between the gas-phase feeding device and the reaction device to control the quantities of the gas-phase material fed to the catalyst bed layers. Alternatively, the allocation proportion K1 can be controlled to be within the above-mentioned range by other means. The flow control devices may be any elements that can realize flow control. Preferably, the flow control device(s) in the present invention is (are) flow valve(s) and there are one or more of flow valves.

According to the above-mentioned method provided in the present invention, as long as the temperature and allocation proportion of the first substream fed to the first catalyst bed layer is controlled properly, the object of the present invention can be attained, without taking any other measure to control the temperatures of the rest substreams or the temperatures in the reactors. Therefore, the reaction apparatus for preparing dimethyl ether from methanol provided in the present invention doesn't include a liquid-phase feeding device configured to provide a liquid-phase material to the catalyst bed layers; for example, the reaction apparatus doesn't include a liquid-phase chilling material feeding device.

According to a preferred embodiment of the present invention, in the reaction apparatus for preparing dimethyl ether from methanol, the number of catalyst bed layers is 2~8, preferably is 2~6. The methanol-to-dimethyl ether reaction is an equilibrium reaction, which essentially doesn't depend on the reaction pressure; the conversion rate of methanol is usually 80%~85%, and the reaction result is good as long as the conversion rate is within that range. Usually, the higher the number of catalyst bed layers is, the lower the temperature rise at the stages is, and the lower the hottest-spot temperature is. However, an excessive number of catalyst bed layers may cause increased complexity in the equipment manufacturing, increased complexity in the reactor control, and increased equipment investment. In addition, if the hottest-spot temperature is too low, the reaction will be in an unstable state, and the conversion rate of methanol will be low; if the hottest-spot temperature is increased in a proper range, the conversion rate of methanol will be increased. Usually, when the hottest-spot temperature is higher than 380° C., the reaction will be in an unstable state, temperature runaway may occur easily in the reaction, and the difficulty in temperature control will be increased. Therefore, a key point in the reaction for preparing dimethyl ether is the hottest-spot temperature; hence, an appropriate number of catalyst bed layers must be selected. The hottest-spot temperature is always controlled within 320~383° C., preferably 330~360° C.

The heights of the catalyst bed layer may be the same or different from each other. In view that the feed amounts to the catalyst bed layers in the present invention decrease stage by stage in the reactant stream flow direction, preferably the heights of the catalyst bed layer decrease stage by stage from top to bottom, according to the engineering design principle.

According to a preferred embodiment of the present invention, the reaction device comprises one or more fixed bed reactors, with said a plurality of catalyst bed layers arranged in the one or more fixed bed reactors, preferably, the reaction device comprises one fixed bed reactor, with said a plurality of catalyst bed layers arranged in the same fixed bed reactor; or the reaction device comprises a plurality of fixed bed reactors, with one catalyst bed layer arranged in each fixed bed reactor.

The reaction apparatus for preparing dimethyl ether from methanol provided in the present invention may further comprise one or more temperature measuring devices configured to measure the temperatures of the feeding materials (especially the temperature of the substeam fed to the first catalyst bed layer), the discharging temperatures of the material streams from the catalyst bed layers, and the hottest-spot temperatures in the catalyst bed layers.

In a third aspect of the present invention, a method for preparing olefin from methanol is provided, comprising: preparing dimethyl ether from methanol with the above-mentioned method, and then controlling the product obtained from the previous reaction to react to prepare olefin under conditions for preparing olefin from dimethyl ether.

According to a preferred embodiment of the present invention, the conditions for preparing olefin from dimethyl ether include: the reaction temperature is 390~650° C., preferably is 400~600° C., more preferably is 420~520° C., further more preferably is 450~480° C.; the pressure is 0.01~2 MPaG, preferably is 0.02~1 MPaG, more preferably is 0.05~0.5 MPaG, further more preferably is 0.05~0.1 MPaG; the mass space velocity of the reaction product is 0.01~6 h−1, preferably is 0.05~2 h−1, more preferably is 0.1~4 h−1, further more preferably is 0.5~1 h−1.

In the present invention, unless otherwise stated, in the methanol-to-dimethyl ether reaction, the space velocity of each catalyst bed is the space velocity of each substream F1, F2, . . . , Fn in relation to the corresponding catalyst bed layer BED1, BED2, . . . , BEDn, while in the dimethyl ether-to-olefin reaction, the space velocity is the general space velocity, i.e., the space velocity of all material in relation to all catalyst for preparing olefin from dimethyl ether.

According to a preferred embodiment of the present invention, the reaction for preparing olefin is carried out in a fixed bed reactor that comprises at least two conversion zones, wherein, counted from top to bottom, the first conversion zone comprises gas distribution elements and catalyst bed layers, and the second conversion zone and other conversion zones comprise gas distribution elements, liquid atomization elements, and catalyst bed layers; the reaction of preparing olefin from the product obtained from the previous reaction under the conditions for preparing olefin from dimethyl ether comprises: dividing into the reaction product obtained from the previous reaction into a plurality of streams, heating up the first gas-phase stream and then feeding it via the gas distribution elements into the first conversion zone, while directly feeding the rest gas-phase streams via the gas distribution elements into the second conversion zone and other conversion zones without heating or cooling; and feeding a liquid-phase chilling material via the liquid atomization elements into the second conversion zone and other conversion zones.

Preferably, each conversion zone comprises one catalyst bed layer.

The heights of the catalyst bed layers may be 100~1,000 mm, preferably are 200~600 mm. Preferably, the total height of the catalyst bed layers for preparing olefin from dimethyl ether are 200~6,000 mm, more preferably are 500~3,000 mm. The heights of the catalyst bed layer may be the same or different from each other; preferably, from top to bottom, the heights of the catalyst bed layers increase gradually.

According to a preferred embodiment of the present invention, the weight ratio of the first gas-phase stream to the reaction product is 0.08~0.25, preferably is 0.1~0.2. The amounts of the rest gas-phase streams are preferably equal to each other.

According to a preferred embodiment of the present invention, the method for preparing olefin from methanol provided in the present invention comprises the following steps:

(1) The reactant stream methanol is divided into n substreams, these different substreams are fed into the reaction device for dehydration reaction through the feed ports on the top of the reaction devices or the side feed ports between the catalyst bed layers; in the reactant stream flow direction, the flow rates of the n substreams are F1~Fn, and the allocation proportions Ki in the substreams are Fi/F0, wherein, F0 is the sum of F1~Fn, i is an integer within the range of 1~n, and n is an integer greater than 1; wherein, the temperature T1 of the substream fed to the first catalyst bed layer is controlled within the following range:

$$290-50K1 \le T1 \le 150K1^2 - 271K1 + 397.5$$

wherein, $1 > K1 \ge 0.5$, and T1 is in unit of ° C.;

(2) a part of the reaction product obtained in the step (1) is heated up to a desired temperature and then fed through the top of the reaction device for preparing olefin, the other part of the reaction product is directly divided into a plurality of streams without heating or cooling, and the streams are fed through the side feed ports between the catalyst bed layers of the reaction device for preparing olefin; in addition, a chilling material is fed through the side feed ports between the catalyst bed layers of the reaction device for preparing olefin.

The reaction conditions involved in the steps (1) and (2) correspond to the above-mentioned reaction conditions for preparing dimethyl ether from methanol and reaction conditions for preparing olefin from dimethyl ether respectively. Those conditions have been described above, and will not be detailed anymore here.

In a forth aspect of the present invention, a system for preparing olefin from methanol is provided, comprising a unit for preparing dimethyl ether from methanol and a unit for preparing olefin from dimethyl ether, wherein, a discharge port of the unit for preparing dimethyl ether from methanol communicates with a feed port of the unit for preparing olefin from dimethyl ether, and the unit for preparing dimethyl ether from methanol is the above-mentioned reaction apparatus for preparing dimethyl ether from methanol.

According to the system for preparing olefin from methanol provided in the present invention, the unit for preparing olefin from dimethyl ether may be any apparatus for preparing olefin from dimethyl ether in the prior art. According to a preferred embodiment of the present invention, the unit for preparing olefin from dimethyl ether comprises a reaction device for preparing olefin and a liquid-phase chilling material feeding unit, wherein, the reaction device for preparing olefin comprises at least two conversion zones, wherein, counted from top to bottom, the first conversion zone comprises gas distribution elements and catalyst bed layers, and the second conversion zone and other conversion zones comprise gas distribution elements, liquid atomization elements, and catalyst bed layers; the liquid-phase chilling material feeding unit communicates with the liquid atomization elements and feeds the material to the liquid atomization elements.

Preferably, the system further comprises: a flow control device (preferably flow valve) arranged between the unit for preparing dimethyl ether from methanol and the unit for preparing olefin from dimethyl ether and configured to control the amount of the material from the unit for preparing dimethyl ether from methanol into the conversion zones; and a heater arranged between the unit for preparing dimethyl ether from methanol and the unit for preparing olefin from dimethyl ether and configured to heat up the material entering into the first conversion zone (including the material from the unit for preparing dimethyl ether from methanol and an inert component that is fed selectively), so that the material reaches to a desired temperature (usually is 350~550° C., preferably is 390~500° C.).

Preferably, the conversion zones are in quantity of 2~8 zones, more preferably 3~6 zones.

The catalyst that forms the catalyst bed layers in the reaction device for preparing olefin may be any catalyst suitable for the MTP process, including but not limited to a modified molecular sieve. For example, the modified molecular sieve may be a molecular sieve modified by rare earth metal and phosphate. For example, the rare earth metal may be one or more of Sc, Y, La, Ce, Pr, Nd, Pm, Sm, Eu, Gd, Tb, Dy, Ho, Er, Tm, Yb and Lu. Preferably, the silica-alumina mole ratio of the molecular sieve modified by the rare earth metal and phosphate is 20~1,000, more preferably is 200~500. For example, the modified molecular sieve may be a molecular sieve catalyst in a ZSM series, such as one or more of ZSM-5, ZSM-11, ZSM-12, ZSM-23, and ZSM-35. Specifically, the catalyst may be one or more of SMAP-100 series from SINOPEC Shanghai Research Institute of Petrochemical Technology and MTPROP-1 from Lurgi (a German company).

For the details of the above-mentioned method and apparatus for preparing olefin from dimethyl ether, please see CN103421561A, which is incorporated as a reference in the present invention.

Figure 4:
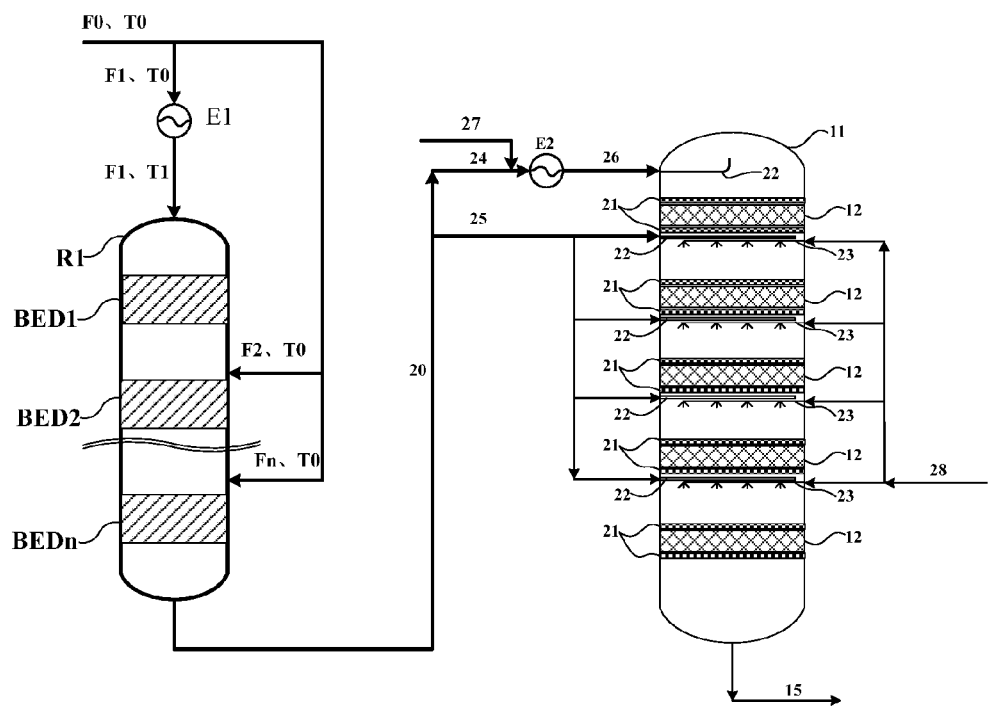
FIG. 4 is a schematic flow chart of an embodiment of the method for preparing olefin from methanol according to the present invention.
Figure 5:
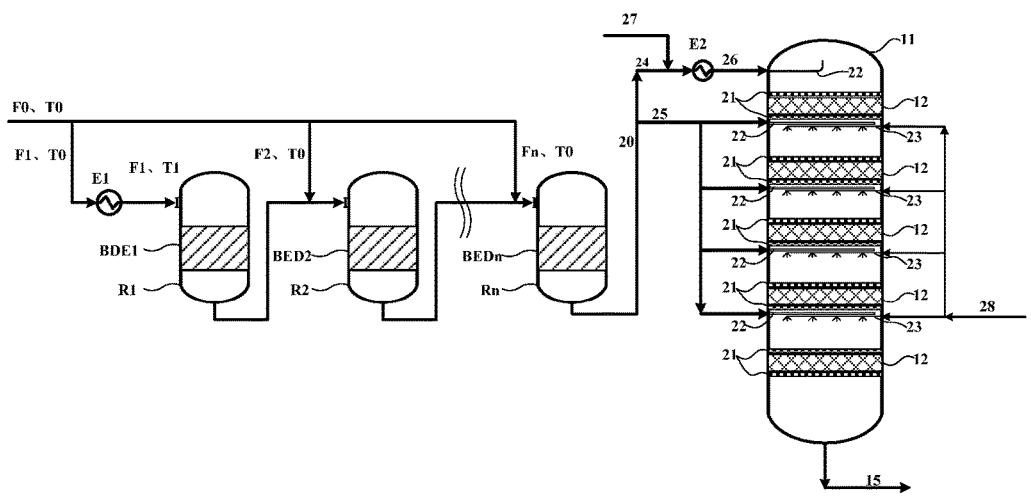
FIG. 5 is a schematic flow chart of another embodiment of the method for preparing olefin from methanol according to the present invention.

According to a preferred embodiment of the present invention, the process flow for preparing olefin from methanol provided in the present invention comprises the steps shown in FIGS. 4 and 5: the raw material methanol (F0, T0) is divided into n substreams in the flow rates of F1, F2, ..., Fn, the first substream is heated up in the heater E1 to temperature T1 and then fed to the first catalyst bed layer BED1 of the fixed bed reactor R1 through the top of the reactor; the rest streams are directly fed through the side feed ports of the reactor to the catalyst bed layers BED2, ..., BEDn respectively without heating or cooling (usually they are still at the temperature T0); after the reaction, the material 20 is discharged through the bottom of the reactor, a part of the material (stream 24) is heated in the heater E2 and then fed via the gas distribution elements 22 in the first conversion zone into the first conversion zone through the top of the reactor for preparing olefin (a MTP reactor), while the other part (stream 25) is divided into a plurality of streams, and the streams are fed into the second conversion zone and other conversion zones via the gas distribution elements 22 in the corresponding conversion zones respectively; a liquid-phase chilling material 28 is divided into a plurality of streams corresponding to the gas-phase streams, and the liquid-phase chilling streams are fed into the second conversion zone and other conversion zones via the liquid atomization elements 23 in the corresponding conversion zones respectively, and contact with the catalyst bed layers 12 to prepare olefin. The obtained product is discharged through the bottom of the reactor (stream 15).

Preferably, an inert component (stream 27) is mixed with the stream 24, heated up, and fed into the first conversion zone (stream 26). For example, the inert component may be alkane added externally, a hydrocarbon mixture obtained through separation and purification of the reaction product, or an inert gas added externally, such as nitrogen. The mass flow ratio of the inert component to the stream 24 is preferably 5~10.

The liquid-phase chilling material 28 may be one or more of water, methanol, and dimethyl ether. The mass flow ratio of the liquid-phase chilling material 28 to the stream 24 is preferably 0.5~1.0.

In the present invention, the gas distribution element may be one of elbow pipe, tubular distributor, arc distributor, and circular distributor, or an assembly of them.

The liquid atomization element preferably is a gas compression atomizer or nozzle.

As shown in FIGS. 4 and 5, the difference between FIG. 4 and FIG. 5 only lies in whether a plurality of catalyst bed layers for the methanol-to-dimethyl ether reaction is loaded in one reactor or a plurality of reactors.

Hereunder the present invention will be further detailed in some examples. However, those examples shall not be deemed as constituting any limitation to the present invention. In the embodiments, the temperatures are in unit of ° C., the outlet temperatures are the results measured after reaction for 24 h, the hottest-spot temperatures are measured with a thermocouple thermometer, and the conversion rate of methanol (X %) is calculated with a formula "conversion rate of methanol=(1−methanol content in the discharged material/methanol content in the feed material)×100%". The yield of propylene (Y %) is equal to the conversion rate of methanol×selectivity of propylene, and the selectivity of propylene is equal to propylene content in the product stream/sum of contents of all substances that contain carbon atoms in the product stream. The contents of the components in the product stream is measured by gas chromatography.

Example 1

Industrial methanol with purity higher than 99 mass % is used as the raw material, the catalyst SMAP-500 from SINOPEC Shanghai Research Institute of Petrochemical Technology is used as the catalyst, altogether 6 catalyst bed layers are deployed (i.e., n=6), the pressure in the fixed bed reactor is 0.5 MPaG, the space velocities of the materials fed to the catalyst bed layers are 3.5 h−1, 2.5 h−1, 2 h−1, 1.5 h−1, 1 h−1 and 1 h−1 respectively, and the process flow shown in FIG. 4 is used for the methanol-to-dimethyl ether reaction, wherein, T0=150° C., F0=1,000 kg/h, F1=700 kg/h, and thereby K1=0.7. Calculated with the formula $290-50K1 \leq T1 \leq 150K1^2-271K1+397.5$, the result is $255 \leq T1 \leq 281.3$; the T1 is set to 260, 275 and 280° C. for the temperature of the material fed to the first reaction zone respectively, $Ki=(1-\Sigma_{i=1}^{i-1}K)\times70\%$ is used for the reaction, and the measured outlet temperatures, hottest-spot temperatures, and conversion rates of methanol in the reaction zones BED 1~BED6 are shown in Table 1.

In the MTP reactor, the catalyst is Catalyst SMAP-100 from SINOPEC Shanghai Research Institute of Petrochemical Technology; altogether 6 catalyst bed layers are deployed; the flows of the gas-phase streams are equal to each other, except for the first stream; the stream 27 is nitrogen added externally at 50° C., the mass flow of the nitrogen is 6 times of the mass flow of the stream 27. The stream 28 is a mixture of water and methanol, in which the water content is 95 mass %, the temperature of the stream 28 is 90° C., and the mass flow of the stream 28 is 0.8 times of the mass flow of the stream 27; the rest reaction conditions and results are shown in Table 2.

TABLE 1

|  | BED1 | BED2 | BED3 | BED4 | BED5 | BED6 | $T_H$ | X % |
| --- | --- | --- | --- | --- | --- | --- | --- | --- |
| T1 = 260 | 307 | 290 | 301 | 314 | 325 | 330 | 330 | 83.98% |
| T1 = 275 | 321 | 301 | 310 | 322 | 333 | 338 | 338 | 83.95% |
| T1 = 280 | 330 | 307 | 316 | 328 | 339 | 340 | 340 | 83.92% |

TABLE 2

|  | $T_{20}$ | $F_{24}:F_{20}$ | $T_{26}$ | $T_H$ | P | S.V. | C.L. | Y % | $C_{CH3OH}$ |
|---|---|---|---|---|---|---|---|---|---|
| T1 = 260 | 330 | 0.10 | 452 | 463 | 0.08 | 0.5 | 1620 | 62.8% | 190 ppm |
| T1 = 275 | 338 | 0.15 | 461 | 475 | 0.1 | 0.7 | 1563 | 61.4% | 305 ppm |
| T1 = 280 | 340 | 0.20 | 476 | 483 | 0.05 | 1.0 | 1345 | 60.2% | 315 ppm |

Note:
$T_H$ means hottest-spot temperature,
$T_{20}$ means the temperature of stream 20,
$T_{26}$ means the temperature of stream 26,
$F_{24}:F_{20}$ means Stream 24:Stream 20 mass flow ratio,
P means the pressure in the reactor for preparing olefin in the unit of MPaG,
S.V. is the general space velocity of the total reactant for preparing olefin in the unit of $h^{-1}$,
C.L. means the catalyst life of the catalyst in the reaction for preparing olefin, and
$C_{CH3OH}$ means the methanol content in the stream 15, the same below.

Example 2

Industrial methanol with purity higher than 99 mass % is used as the raw material, the catalyst SMAP-500 from SINOPEC Shanghai Research Institute of Petrochemical Technology is used as the catalyst, altogether 3 catalyst bed layers are deployed (i.e., n=4), the pressure in the fixed bed reactor is 0.1 MPaG, the space velocities of the materials fed to the catalyst bed layers are 3 h−1, 2 h−1, 1.5 h−1 and 1 h−1 respectively, and the process flow shown in FIG. 4 is used for the methanol-to-dimethyl ether reaction, wherein, T0=180° C., F0=1,000 kg/h, F1=800 kg/h, and thereby K1=0.8. Calculated with the 290−50K1≤T1≤150K1$^2$−271K1+397.5, the result is 250≤T1≤276.7; the T1 is set to 255, 265 and 275° C. for the temperature of the material fed to the first reaction zone respectively, Ki=(1−$\Sigma_{i=1}^{i-1}$K)×90% is used for the reaction, and the measured outlet temperatures, hottest-spot temperatures, and conversion rates of methanol in the reaction zones BED 1~BED3 are shown in Table 3.

In the MTP reactor, the catalyst is Catalyst SMAP-100 from SINOPEC Shanghai Research Institute of Petrochemical Technology; altogether 6 catalyst bed layers are deployed; the flows of the gas-phase streams are equal to each other, except the first stream; the stream 27 is nitrogen added externally at 20° C., the mass flow of the nitrogen is 8 times of the mass flow of the stream 27. The stream 28 is a mixture of water and methanol, in which the water content is 90 mass %, the temperature of the stream 28 is 95° C., and the mass flow of the stream 28 is 0.6 times of the mass flow of the stream 27; the rest reaction conditions and results are shown in Table 4.

TABLE 3

|  | BED1 | BED2 | BED3 | $T_H$ | X % |
|---|---|---|---|---|---|
| T1 = 255 | 307 | 290 | 330 | 330 | 84.02% |
| T1 = 265 | 321 | 301 | 335 | 335 | 83.91% |
| T1 = 275 | 330 | 307 | 340 | 340 | 83.85% |

TABLE 4

|  | $T_{20}$ | $F_{24}:F_{20}$ | $T_{26}$ | $T_H$ | P | S.V. | C.L. | Y % | $C_{CH3OH}$ |
|---|---|---|---|---|---|---|---|---|---|
| T1 = 255 | 330 | 0.1 | 452 | 483 | 0.08 | 0.5 | 1610 | 62.6% | 200 ppm |
| T1 = 265 | 335 | 0.12 | 459 | 495 | 0.1 | 0.7 | 1570 | 61.6% | 255 ppm |
| T1 = 275 | 340 | 0.15 | 480 | 503 | 0.1 | 1.0 | 1348 | 60.5% | 295 ppm |

Example 3

Industrial methanol with purity higher than 99 mass % is used as the raw material, the catalyst SMAP-500 from SINOPEC Shanghai Research Institute of Petrochemical Technology is used as the catalyst, altogether 5 catalyst bed layers are deployed (i.e., n=5), the pressure in the fixed bed reactor is 2 MPaG, the space velocities of the materials fed to the catalyst bed layers are 2 h−1, and the process flow shown in FIG. 4 is used for the methanol-to-dimethyl ether reaction, wherein, T0=165° C., F0=1,000 kg/h, F1=750 kg/h, and thereby K1=0.75. Calculated with the formula 290−50K1≤T1≤150K1$^2$−271K1+397.5, the result is 252.5≤T1≤278.6; the T1 is set to 252.5, 265, and 278.6° C. for the temperature of the material fed to the first reaction zone respectively, Ki=(1−$\Sigma_{i=1}^{i-1}$K)×95% is used for the reaction, and the measured outlet temperatures, hottest-spot temperatures, and conversion rates of methanol in the reaction zones BED1~BED5 are shown in Table 5.

In the MTP reactor, the catalyst is Catalyst SMAP-100 from SINOPEC Shanghai Research Institute of Petrochemical Technology; altogether 4 catalyst bed layers are deployed; the flows of the gas-phase streams are equal to each other, except the first stream; the stream 27 is nitrogen added externally at 40° C., the mass flow of the nitrogen is 6 times of the mass flow of the stream 27. The stream 28 is a mixture of water and methanol, in which the water content is 98 mass %, the temperature of the stream 28 is 90° C., and the mass flow of the stream 28 is 1.2 times of the mass flow of the stream 27; the rest reaction conditions and results are shown in Table 6.

TABLE 5

|  | BED1 | BED2 | BED3 | BED4 | BED5 | $T_H$ | X % |
|---|---|---|---|---|---|---|---|
| T1 = 252.5 | 307 | 290 | 301 | 314 | 333 | 333 | 84.22% |
| T1 = 265 | 321 | 301 | 310 | 322 | 341 | 341 | 84.02% |
| T1 = 278.6 | 330 | 307 | 316 | 347 | 339 | 347 | 83.90% |

TABLE 6

|  | $T_{20}$ | $F_{24}:F_{20}$ | $T_{26}$ | $T_H$ | P | S.V. | C.L. | Y % | $C_{CH3OH}$ |
|---|---|---|---|---|---|---|---|---|---|
| T1 = 252 | 333 | 0.15 | 452 | 473 | 0.08 | 0.5 | 1590 | 62.6% | 205 ppm |
| T1 = 265 | 341 | 0.15 | 462 | 485 | 0.1 | 0.7 | 1568 | 61.8% | 320 ppm |
| T1 = 278 | 347 | 0.20 | 476 | 493 | 0.1 | 1.0 | 1355 | 60.5% | 340 ppm |

Example 4

Dimethyl ether and olefin are prepared from methanol with the method described in the Example 1, except that F1=600 kg/h, and thereby K1=0.6. Calculated with the formula $290-50K1 \leq T1 \leq 150K1^2-271K1+397.5$, the result is $260 \leq T1 \leq 288.9$; T1 is set to 260, 275 and 285° C. for the temperature of the material fed to the first reaction zone respectively, and the measured outlet temperatures, hottest-spot temperatures, and conversion rates of methanol in the reaction zones BED1~BED6 are shown in Table 7. The reaction conditions for preparing olefin from dimethyl ether and the results are shown in Table 8.

TABLE 7

|  | BED1 | BED2 | BED3 | BED4 | BED5 | BED6 | $T_H$ | X % |
|---|---|---|---|---|---|---|---|---|
| T1 = 260 | 307 | 290 | 301 | 314 | 325 | 331 | 331 | 83.84% |
| T1 = 275 | 321 | 301 | 310 | 322 | 333 | 335 | 335 | 83.85% |
| T1 = 285 | 330 | 307 | 316 | 328 | 339 | 342 | 342 | 83.88% |

TABLE 8

|  | $T_{20}$ | $F_{24}:F_{20}$ | $T_{26}$ | $T_H$ | P | S.V. | C.L. | Y % | $C_{CH3OH}$ |
|---|---|---|---|---|---|---|---|---|---|
| T1 = 260 | 331 | 0.10 | 452 | 480 | 0.08 | 0.5 | 1580 | 61.2% | 200 ppm |
| T1 = 275 | 335 | 0.15 | 429 | 490 | 0.1 | 0.7 | 1483 | 58.8% | 325 ppm |
| T1 = 285 | 342 | 0.20 | 396 | 500 | 0.05 | 1.0 | 1265 | 56.0% | 360 ppm |

Example 5

Dimethyl ether and olefin are prepared from methanol with the method described in the Example 4, except for $Ki=(1-\Sigma_{i=1}^{i-1}K)\times60\%$ is used for the reaction; the measured outlet temperatures, hottest-spot temperatures, and conversion rates of methanol in the reaction zones BED1~BED6 are shown in Table 9. The reaction conditions for preparing olefin from dimethyl ether and the results are shown in Table 10.

TABLE 9

|  | BED1 | BED2 | BED3 | BED4 | BED5 | BED6 | $T_H$ | X % |
|---|---|---|---|---|---|---|---|---|
| T1 = 260 | 307 | 290 | 301 | 314 | 325 | 333 | 333 | 83.82% |
| T1 = 275 | 321 | 301 | 310 | 322 | 333 | 341 | 341 | 83.81% |
| T1 = 285 | 330 | 307 | 316 | 328 | 339 | 347 | 347 | 83.80% |

TABLE 10

|  | $T_{20}$ | $F_{24}:F_{20}$ | $T_{26}$ | $T_H$ | P | S.V. | C.L. | Y % | $C_{CH3OH}$ |
|---|---|---|---|---|---|---|---|---|---|
| T1 = 260 | 333 | 0.10 | 452 | 483 | 0.08 | 0.5 | 1520 | 60.8% | 210 ppm |
| T1 = 275 | 341 | 0.15 | 429 | 495 | 0.1 | 0.7 | 1463 | 58.4% | 345 ppm |
| T1 = 285 | 347 | 0.20 | 446 | 503 | 0.05 | 1.0 | 1245 | 55.2% | 400 ppm |

Example 6

Dimethyl ether and olefin are prepared from methanol with the method described in the Example 1, except that n=4, F1=900 kg/h, and thereby K1=0.9. Calculated with the formula $290-50K1 \leq T1 \leq 150K1^2-271K1+397.5$, the result is $245 \leq T1 \leq 275.1$, and T1 is set to 245, 260 and 275° C. for the temperature of the material fed to the first reaction zone respectively. The measured outlet temperatures, hottest-spot temperatures, and conversion rates of methanol in the reaction zones BED1~BED4 are shown in Table 11, and the reaction conditions for preparing olefin from dimethyl ether and the results are shown in Table 12.

TABLE 11

|  | BED1 | BED2 | BED3 | BED4 | $T_H$ | X % |
|---|---|---|---|---|---|---|
| T1 = 245 | 305 | 326 | 347 | 360 | 360 | 83.90% |
| T1 = 260 | 318 | 338 | 358 | 372 | 372 | 83.85% |
| T1 = 275 | 330 | 350 | 370 | 383 | 383 | 83.80% |

TABLE 12

| | $T_{20}$ | $F_{24}$:$F_{20}$ | $T_{26}$ | $T_H$ | P | S.V. | C.L. | Y % | $C_{CH3OH}$ |
|---|---|---|---|---|---|---|---|---|---|
| T1 = 245 | 360 | 0.10 | 452 | 483 | 0.08 | 0.5 | 1540 | 60.8% | 250 ppm |
| T1 = 260 | 372 | 0.15 | 429 | 495 | 0.1 | 0.7 | 1468 | 58.8% | 355 ppm |
| T1 = 275 | 383 | 0.20 | 396 | 503 | 0.05 | 1.0 | 1248 | 56.9% | 420 ppm |

Example 7

Dimethyl ether and olefin are prepared from methanol with the method described in the Example 6, except that n=2; the measured outlet temperatures, hottest-spot temperatures, and conversion rates of methanol in the reaction zones BED1~BED2 are shown in Table 13, and the reaction conditions for preparing olefin from dimethyl ether and the results are shown in Table 14.

TABLE 13

| | BED1 | BED2 | $T_H$ | X % |
|---|---|---|---|---|
| T1 = 245 | 342 | 360 | 360 | 83.83% |
| T1 = 260 | 355 | 372 | 372 | 83.82% |
| T1 = 275 | 368 | 383 | 383 | 83.81% |

TABLE 14

| | $T_{20}$ | $F_{24}$:$F_{20}$ | $T_{26}$ | $T_H$ | P | S.V. | C.L. | Y % | $C_{CH3OH}$ |
|---|---|---|---|---|---|---|---|---|---|
| T1 = 245 | 364 | 0.10 | 445 | 482 | 0.08 | 0.7 | 1860 | 60.7% | 220 ppm |
| T1 = 260 | 377 | 0.15 | 455 | 486 | 0.6 | 1.2 | 1402 | 57.1% | 350 ppm |
| T1 = 275 | 390 | 0.20 | 465 | 492 | 1.6 | 1.8 | 1086 | 54.8% | 440 ppm |

Example 8

Dimethyl ether and olefin are prepared from methanol with the method described in the Example 7, except that aqueous methanol with 95 mass % methanol content and 5 mass % water content is used as the raw material; the measured outlet temperatures, hottest-spot temperatures, and conversion rates of methanol in the reaction zones BED1~BED2 are shown in Table 15, and the reaction conditions for preparing olefin from dimethyl ether and the results are shown in Table 16.

TABLE 15

| | BED1 | BED2 | $T_H$ | X % |
|---|---|---|---|---|
| T1 = 245 | 336 | 301 | 336 | 83.85% |
| T1 = 260 | 349 | 314 | 349 | 83.84% |
| T1 = 275 | 363 | 326 | 363 | 83.82% |

TABLE 16

| | $T_{20}$ | $F_{24}$:$F_{20}$ | $T_{26}$ | $T_H$ | P | S.V. | C.L. | Y % | $C_{CH3OH}$ |
|---|---|---|---|---|---|---|---|---|---|
| T1 = 245 | 336 | 0.10 | 455 | 482 | 0.08 | 0.7 | 1900 | 64.8% | 98 ppm |
| T1 = 260 | 349 | 0.15 | 455 | 498 | 0.6 | 1.2 | 1532 | 62.4% | 250 ppm |
| T1 = 275 | 363 | 0.20 | 455 | 509 | 1.6 | 1.8 | 1340 | 61.2% | 300 ppm |

It can be seen from the comparison between the Tables 13-14 and the Tables 15-16: increased water content is beneficial for decreasing the hottest-spot temperature. In this embodiment, the water content is 5 mass %; thus, the hottest-spot temperature is decreased by about 20° C.

Example 9

Dimethyl ether and olefin are prepared from methanol with the method described in the Example 1, except that K1=0.8, T1 is 250, 263 and 276° C. respectively; and Ki=$(1-\Sigma_{i=1}^{i-1}K)\times 60\%$. The measured outlet temperatures, hottest-spot temperatures, and conversion rates of methanol in the reaction zones BED1~BED2 are shown in Table 17, and the reaction conditions for preparing olefin from dimethyl ether and the results are shown in Table 18.

TABLE 17

|  | BED1 | BED2 | BED3 | BED4 | BED5 | BED6 | $T_H$ | X % |
|---|---|---|---|---|---|---|---|---|
| T1 = 250 | 293 | 297 | 316 | 332 | 343 | 352 | 352 | 83.83% |
| T1 = 263 | 263 | 307 | 325 | 341 | 353 | 361 | 361 | 83.82% |
| T1 = 276 | 318 | 318 | 335 | 350 | 362 | 370 | 370 | 83.81% |

TABLE 18

|  | $T_{20}$ | $F_{24}{:}F_{20}$ | $T_{26}$ | $T_H$ | P | S.V. | C.L. | Y % | $C_{CH3OH}$ |
|---|---|---|---|---|---|---|---|---|---|
| T1 = 250 | 352 | 0.085 | 475 | 482 | 0.07 | 0.7 | 1420 | 60.5% | 220 ppm |
| T1 = 263 | 361 | 0.14 | 462 | 488 | 0.5 | 2.0 | 1008 | 53.4% | 350 ppm |
| T1 = 276 | 370 | 0.19 | 450 | 489 | 1.6 | 6.0 | 800 | 47.2% | 365 ppm |

Example 10

Dimethyl ether and olefin are prepared from methanol with the method described in the Example 1, except that n=4, T1 is 255, 268 and 281° C. respectively; and $K_i = (1 - \Sigma_{i=1}^{i-1} K) \times 50\%$. The measured outlet temperatures, hottest-spot temperatures, and conversion rates of methanol in the reaction zones BED1~BED4 are shown in Table 19, and the reaction conditions for preparing olefin from dimethyl ether and the results are shown in Table 20.

TABLE 19

|  | BED1 | BED2 | BED3 | BED4 | $T_H$ | X % |
|---|---|---|---|---|---|---|
| T1 = 255 | 323 | 330 | 340 | 343 | 343 | 83.82% |
| T1 = 268 | 335 | 340 | 349 | 351 | 351 | 83.81% |
| T1 = 281 | 347 | 350 | 358 | 359 | 359 | 83.80% |

TABLE 20

|  | $T_{20}$ | $F_{24}{:}F_{20}$ | $T_{26}$ | $T_H$ | P | S.V. | C.L. | Y % | $C_{CH3OH}$ |
|---|---|---|---|---|---|---|---|---|---|
| T1 = 255 | 343 | 0.09 | 451 | 482 | 0.03 | 0.8 | 1820 | 60.8% | 180 ppm |
| T1 = 268 | 351 | 0.16 | 431 | 498 | 0.25 | 1.5 | 1032 | 54.4% | 250 ppm |
| T1 = 281 | 359 | 0.18 | 393 | 509 | 0.6 | 1.2 | 960 | 52.2% | 275 ppm |

Example 11

Dimethyl ether and olefin are prepared from methanol with the method described in the Example 8, except that K1=0.95, T1 is 243, 259 and 275° C. respectively. The measured outlet temperatures, hottest-spot temperatures, and conversion rates of methanol in the reaction zones BED1~BED2 are shown in Table 21, and the reaction conditions for preparing olefin from dimethyl ether and the results are shown in Table 22.

TABLE 21

|  | BED1 | BED2 | $T_H$ | X % |
|---|---|---|---|---|
| T1 = 243 | 338 | 364 | 364 | 83.83% |
| T1 = 259 | 352 | 377 | 377 | 83.82% |
| T1 = 275 | 366 | 390 | 390 | 83.81% |

TABLE 22

|  | $T_{20}$ | $F_{24}{:}F_{20}$ | $T_{26}$ | $T_H$ | P | S.V. | C.L. | Y % | $C_{CH3OH}$ |
|---|---|---|---|---|---|---|---|---|---|
| T1 = 243 | 364 | 0.10 | 445 | 482 | 0.08 | 0.7 | 1860 | 61.7% | 100 ppm |
| T1 = 259 | 377 | 0.16 | 455 | 486 | 0.6 | 1.2 | 1402 | 57.1% | 150 ppm |
| T1 = 275 | 390 | 0.20 | 465 | 492 | 1.6 | 1.8 | 1086 | 51.8% | 350 ppm |

Comparative Example 1

The methanol-to-dimethyl ether reaction is carried out through the process flow shown in FIG. 1 with the method and reactor disclosed in U.S. Pat. No. 2,014,408. The measured outlet temperatures, hottest-spot temperatures, and conversion rates of methanol in the reaction zones are shown in Table 23.

The reactor used for preparing propylene and other reaction conditions are the same as those in the Example 7 and the reaction conditions for preparing olefin from dimethyl ether and the results are shown in Table 24.

TABLE 23

| Inlet Temperature | Outlet Temperature | $T_H$ | X % |
|---|---|---|---|
| 245 | 372 | 372 | 83.82% |
| 260 | 384 | 384 | 83.83% |
| 275 | 397 | 397 | 83.81% |

TABLE 24

| Inlet Temperature | $T_{20}$ | $F_{24}:F_{20}$ | $T_{26}$ | $T_H$ | P | S.V. | C.L. | Y % | $C_{CH3OH}$ |
|---|---|---|---|---|---|---|---|---|---|
| 245 | 364 | 0.10 | 445 | 482 | 0.08 | 0.7 | 860 | 51.7% | 300 ppm |
| 260 | 377 | 0.15 | 455 | 486 | 0.6 | 1.2 | 602 | 47.1% | 0.09 wt % |
| 275 | 390 | 0.20 | 465 | 492 | 1.6 | 1.8 | 586 | 41.8% | 1.63 wt % |

It can be seen from the comparison between the Tables 19-20 and the Tables 23-24: to attain the same conversion rate of methanol, under the condition of the same inlet temperature T1, the hottest-spot temperatures in the Comparative Example 1 are higher than those in the present invention by about 12° C.

Comparative Example 2

Dimethyl ether is prepared from methanol with the method described in the Example 7, except that the allocation proportion of the first material stream is set to 0.1, 0.15, 0.2 and 0.3 respectively; and the inlet temperature is set to 290° C., 285° C., 280° C. and 275° C. respectively. The measured outlet temperatures, hottest-spot temperatures, and conversion rates of methanol in the reaction zones are shown in Table 25, and the reaction conditions for preparing olefin from dimethyl ether and the results are shown in Table 26.

TABLE 25

|  | BED1 | BED2 | $T_H$ | X % |
|---|---|---|---|---|
| T1 = 290 | 300 | 185 | 300 | 14.4% |
| T1 = 285 | 303 | 193 | 303 | 16.2% |
| T1 = 280 | 304 | 201 | 304 | 17.2% |
| T1 = 275 | 306 | 217 | 306 | 19.3% |

TABLE 26

|  | $T_{20}$ | $F_{24}:F_{20}$ | $T_{26}$ | $T_H$ | P | S.V. | C.L. | Y % | $C_{CH3OH}$ |
|---|---|---|---|---|---|---|---|---|---|
| T1 = 290 | 185 | 0.10 | 450 | 505 | 0.08 | 0.8 | 242 | 15.8% | 6.5 wt % |
| T1 = 285 | 193 | 0.16 | 460 | 516 | 0.6 | 1.2 | 223 | 14.1% | 8.6 wt % |
| T1 = 280 | 201 | 0.20 | 470 | 527 | 1.5 | 2.0 | 190 | 13.2% | 10.3 wt % |
| T1 = 275 | 217 | 0.08 | 480 | 535 | 1.8 | 1.5 | 186 | 13.5% | 10.2 wt % |

It is seen from the comparison between the results in the above table, under the condition of the same other reaction conditions, in the Comparative Example 2, the allocation proportion of the first material stream is not controlled within the range of 0.5≤K1<1; consequently, though the inlet temperatures are similar to those in the embodiments, a great deal of methanol reacts in the follow-up catalyst bed layers, because the K1 is too small. However, the heat released from the methanol-to-dimethyl ether reaction in the first catalyst bed layer is not enough to maintain the follow-up reaction at a smooth reaction temperature; consequently, the temperature of the reaction for preparing dimethyl ether is severely decreased, and can't reach the reaction temperature required for stable reaction. Hence, the conversion rate of methanol is severely decreased. In addition, the poor result of the reaction for preparing dimethyl ether has a direct impact on the follow-up reaction for preparing olefin. Though the temperature of the stream in the reaction for preparing olefin is near an optimal value, the reaction result is still poor, the life of the catalyst for preparing olefin is severely shortened, the yield of propylene is severely decreased, and the content of unreacted methanol is increased severely.

Comparative Example 3

Dimethyl ether is prepared from methanol with the method described in the Example 7, except that T1 is set to 230 and 320° C. for the temperature of the material fed to the first reaction zone; the measured outlet temperatures, hottest-spot temperatures, and conversion rates of methanol in the reaction zones BED1~BED2 are shown in Table 27.

TABLE 27

|  | BED1 | BED2 | $T_H$ | X % |
|---|---|---|---|---|
| T1 = 230 | 272 | 288 | 288 | 23.3% |
| T1 = 320 | 415 | 424 | 424 | 89.6% |

According to the method described in the present invention, it is seen that the feeding temperature T1 in the present invention is within the range of 245~289° C. In contrast, in the comparative examples, T1 is set to 230 and 320° C., out of the above-mentioned range. It can be seen from the results in Table 27: when the T1 is 230° C., the hottest-spot temperature is too low for the reaction to initiate, and a great deal of methanol is not converted; when the T1 is 320° C., the hottest-spot temperature is too high, beyond the temperature limit that can be endured by the catalyst in the reaction beds, resulting in temperature runaway and shortened catalyst life; in that case, the conversion rate of methanol is very high, mainly incurred by a subsidiary reaction between the hydrogen gas generated from a great deal of decomposed methanol and carbon dioxide, but the quantity of produced dimethyl ether is very small.

It is proven in experiments that the service life of the catalyst used for preparing dimethyl ether is longer than 3 years, usually is 3-5 years, when the method disclosed in the present invention is used. The service life of the catalyst is longer by about 30% than the service life of the catalyst for preparing dimethyl ether in the methods used in the comparative examples.

While some preferred embodiments of the present invention are described above, the present invention is not limited to the details in those embodiments. Those skilled in the art can make modifications and variations to the method of the present invention, without departing from the spirit of the present invention. However, all these modifications and variations shall be deemed as falling into the protected scope of the present invention.

In addition, it should be appreciated that the technical features described in the above embodiments can be combined in any appropriate manner, provided that there is no conflict among the technical features in the combination. To avoid unnecessary iteration, such possible combinations are not described here in the present invention.

Moreover, different embodiments of the present invention can be combined freely as required, as long as the combinations don't deviate from the ideal and spirit of the present invention. However, such combinations shall also be deemed as falling into the scope disclosed in the present invention.

We claim:

1. A method for preparing dimethyl ether from methanol carried out in a reaction device arranged with a plurality of catalyst bed layers connected in series, which method comprising:

dividing a reactant stream containing methanol into n substreams, n being an integer greater than 2, and feeding the n substreams into the reaction device through top feed port or side feed ports between catalyst bed layers of the reaction device to undergo a methanol-to-dimethyl ether reaction;

wherein, according to flow directions of the reactant stream, the n substreams each have a flow rate $F1 \sim Fn$, respectively, allocation proportions $Ki$ of the reactant in the substreams are $Fi/F0$, $F0$ being the sum of $F1 \sim Fn$, i being an integer in the range of $1 \sim n$, and n being an integer greater than 2, and wherein the substream fed into the first catalyst bed layer has a temperature T1 that is controlled within the following range:

$$290-50K1 \leq T1 \leq 150K1^2 - 271K1 + 397.5$$

where $1 > K1 \geq 0.5$, and T1 is in unit of ° C.

2. The method for preparing dimethyl ether from methanol according to claim 1, wherein $2 \leq n \leq 8$.

3. The method for preparing dimethyl ether from methanol according to claim 1, wherein $0.95 \geq K1 \geq 0.6$.

4. The method for preparing dimethyl ether from methanol according to claim 1, wherein $1 > K1 \geq 0.6$.

5. The method for preparing dimethyl ether from methanol according to claim 1, wherein the allocation proportion $Ki$ of the reactant in the substream i $$Ki \geq \left(1 - \sum_{i=1}^{i-1} K_i\right) \times 50\%,$$

wherein $i \neq 1$.

6. The method for preparing dimethyl ether from methanol according to claim 1, wherein the number of the catalyst bed layers is greater than or equal to n.

7. The method for preparing dimethyl ether from methanol according to claim 1, wherein the reaction device comprises one or more fixed bed reactors, with said a plurality of catalyst bed layers arranged in the one or more fixed bed reactors.

* * * * *